United States Patent [19]

Sanderson et al.

[11] Patent Number: 5,191,139
[45] Date of Patent: Mar. 2, 1993

[54] PROCESS FOR OLIGOMERIZING OLEFINS USING SULFATE-ACTIVATED GROUP IV OXIDES

[75] Inventors: John R. Sanderson, Leander; John F. Knifton; John M. Larkin, both of Austin, all of Tex.

[73] Assignee: Texaco Chemical Company, White Plains, N.Y.

[21] Appl. No.: 787,164

[22] Filed: Nov. 4, 1991

[51] Int. Cl.$^5$ .............................................. C07C 2/10
[52] U.S. Cl. ................................... 585/520; 585/526; 585/530; 502/349
[58] Field of Search ....................... 585/520, 526, 530; 502/349

[56] References Cited

U.S. PATENT DOCUMENTS

| | | | |
|---|---|---|---|
| 4,048,109 | 9/1977 | Ryu | 252/442 |
| 4,108,920 | 8/1978 | Ryu | 585/530 |
| 4,110,410 | 8/1978 | Ryu | 585/572 |
| 4,476,243 | 10/1984 | Dombro | 502/236 |
| 4,826,804 | 5/1989 | Shamshoum | 502/214 |
| 4,831,202 | 5/1989 | Guisti et al. | 585/533 |
| 4,962,262 | 10/1990 | Winter et al. | 585/512 |
| 5,003,125 | 3/1991 | Guisti et al. | 585/530 |

OTHER PUBLICATIONS

Arata, Hino, and Yamagata, "Acidity and Catalytic Activity of Zirconium and Titanium Sulfates Heat-Treated at High-Treated Temperature. Solid Superacid Catalysts":, Bull. Chem. Soc. Jpn., vol. 63, No. 1, pp. 244-246 (1990).

Tanabe, Hattori, and Yamaguchi, "Surface Properties of Solid Superacids," Critical Reviews in Surface Chemistry, vol. 1, issue 1, (1990).

Primary Examiner—Asok Pal
Assistant Examiner—P. Achutamurthy
Attorney, Agent, or Firm—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using a sulfate-activated Group IV oxide particularly zirconium dioxide, as the catalyst.

15 Claims, No Drawings

PROCESS FOR OLIGOMERIZING OLEFINS USING SULFATE-ACTIVATED GROUP IV OXIDES

BACKGROUND OF THE INVENTION

1. Field of the Invention

The invention relates to the preparation of synthetic lubricant base stocks, and more particularly to synthetic lubricant base stocks made by oligomerizing linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication, and permit longer drain intervals with less oil vaporization loss between oil changes, than mineral oil base stocks.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of a base stock is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a less hazardous catalyst would be a substantial improvement in the art.

Applicants have discovered, surprisingly, that a high conversion of olefin to oligomer may be obtained by contacting the olefin with a catalyst consisting of a sulfate-activated Group IV oxide, such as sulfate-activated titanium dioxide or sulfate-activated zirconium dioxide. Moreover, the process of the present invention results in a high percentage of dimers, i.e., a high dimer to trimer ratio. A high proportion of dimers is often desirable when preparing a synthetic lubricant base stock from olefins having about 14 or more carbon atoms. In the absence of the high dimer to trimer ratio obtained using the present invention, a synthetic lubricant base stock prepared from olefins having about 14 or more carbon atoms would contain a higher percentage of high molecular weight oligomers and may have too great a viscosity for some applications. In addition to being excellent catalysts, the sulfate-activated oxides used in the present invention are less hazardous and more easily handled than $BF_3$.

SUMMARY OF THE INVENTION

The invention relates to a process for the preparation of oligomers, comprising contacting at elevated temperature (1) a linear olefin containing from 10 to 24 carbon atoms with (2) a catalytically effective amount of a sulfate-activated Group IV oxide. The invention further relates to a process for the preparation of oligomers, comprising oligomerizing a linear olefin containing from 10 to 24 carbon atoms in the presence of a catalytically effective amount of a sulfate-activated Group IV oxide at a temperature in the range of about 50° C. to about 300° C. and at a pressure of about atmospheric to about 1000 psig. The invention also relates to a process for the preparation of oligomers, comprising oligomerizing a linear olefin containing from 14 to 18 carbon atoms in the presence of a catalytically effective amount of a Group IV oxide selected from the group consisting of titanium dioxide and zirconium dioxide, which Group IV oxide has been (1) treated with a sulfur-containing compound selected from the group consisting of ammonium sulfate, ammonium hydrogen sulfate, sulfuric acid, sulfur dioxide, sulfur trioxide, and hydrogen sulfide and (2) calcined at a temperature greater than about 500° C., and wherein the olefin is oligomerized at a temperature in the range of about 120° C. to about 250° C. and at a pressure of about atmospheric to about 1000 psig.

DESCRIPTION OF THE PREFERRED EMBODIMENTS

The olefin monomer feed stocks used in the present invention may be selected from compounds comprising (1) alpha-olefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 14 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization reaction may be represented by the following general equation:

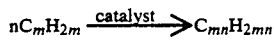

where n represents moles of monomer and m represents the number of carbon atoms in the monomer. Thus, the oligomerization of 1-decene may be represented as follows:

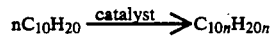

The reaction occurs sequentially. Initially, olefin monomer reacts with olefin monomer to form dimers. Some of the dimers that are formed then react with additional olefin monomers to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalyst used in the present inventive process is a sulfate-activated catalyst. In one embodiment, the sulfate-activated catalyst may be prepared by treating a Group IV oxide with a sulfate-containing compound. Preferably, the sulfate-containing compound is selected from the group consisting of ammonium sulfate, ammonium hydrogen sulfate, sulfuric acid, sulfur trioxide, sulfur dioxide and hydrogen sulfide. Especially preferred sulfating agents are ammonium sulfate and sulfuric acid. Said agents may be employed neat, or as an aqueous, ketonic, alcoholic, or ether solution, but preferably as an aqueous solution. Said sulfating agents also may be employed as mixtures of the sulfating agents listed above. Excess sulfating agent may be removed by a number of procedures, including filtration and evaporation.

Preferably, the sulfated Group IV oxide is then calcined prior to use as an oligomerization catalyst. Calcination in air or in an inert gas environment, such as nitrogen, may be conducted at a temperature of at least 100° C., but below the temperature at which thermal destruction leads to catalyst deactivation. The optimal temperature range can be determined by routine experimentation for a particular catalyst. Typically, the sulfated catalyst is calcined for about 1 to 24 hours at a temperature of from about 500° to 800° C. Good results were achieved, for example, for the ammonium sulfate on zirconia catalyst by calcining at 625°–750° C., for 15 hours, in a stream of nitrogen. Temperatures above 900° C. should be avoided.

Suitable Group IV oxides used in conjunction with said sulfur-containing compounds include, for example, the oxides of silicon, titanium, zirconium, hafnium, germanium, tin, and lead, as well as combinations thereof. Particularly preferred are oxides of titanium and zirconium, such as the anatase or rutile forms of titania and zirconia.

In a more specific embodiment, the Group IV oxide is treated with sulfuric acid by adding said acid neat or, if desired, diluted with distilled water, to the oxide extrudates. The slurry is then mixed for about to 24 hours, filtered, washed, and calcined in a stream of air for about 1 to 24 hours. The prepared sulfuric acid-treated oxide should then have a titratable acidity of at least 0.1 meq/g.

The weight percent of sulfuric acid to Group IV oxide should be such that the concentration of the sulfur in the formulated catalyst is in the range of about 0.1 wt. % to 30 wt. %, although concentrations outside this range also may be employed.

Generally, the catalyst composition is prepared by impregnating a pre-formed pellet, extrudate or powder. A suitable procedure to be used is to immerse titania pellets, for example, in an aqueous or polar organic solvent solution of the acid, preferably at ambient temperature. Higher temperatures of about 100° C. to about 150° C. may be used, if desired. This treatment should be continued, preferably with agitation, for about 0.1 to about 5 hours. The conditions should be sufficient to permit the solution to penetrate the pores of the titania pellet. The amount of acid solution that is used should be adequate to permit full immersion of the titania pellets. Larger amounts of the solution can be used, if desired, but there is no particular advantage in doing so. At the end of the immersion step, the excess solution can be evaporated from the treated pellets, or the pellets can be removed from the solution and permitted to dry (e.g., in a drying oven).

The Group IV oxide may be in the form of powders pellets, spheres, shapes and extrudates. Titania pellets may be prepared by extrusion or by compaction in conventional pelleting apparatus using a pelleting aid such as graphite. Extrudates which work well include HSA titania carrier extrudate from Norton Company, with a surface area of 51 m²/g, and zirconia extrudates from Norton having a surface area of 77 m²/g.

Cylindrically-shaped catalyst pellets having a diameter essentially equal to the length thereof can be employed. Diameters ranging from about 0.794 mm (1/32 inch) to about 9.525 mm (⅜ inch) possess desirable dimensions. The shape and dimensions of the pellets are not critical to the present invention; pellets of any suitable shape and dimensions may be used.

When cylindrical pellets of catalyst of the type described above are used, the liquid hourly space velocity may be varied within wide limits (e.g., 0.1 to 10) in order to obtain a desired rate of conversion. Normally, space velocities of about 0.5 to 2 LHSV will be employed.

Preferably, the pelleted catalyst compositions used in the present inventive process are employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc., in order to obtain a desired rate of reaction and, hence, a desired percentage of conversion of the reactants. In a continuous process, it is not necessary to drive the reaction to completion, because unreacted feedstock components may be recycled to the reactor.

The catalyst compositions of the present invention are advantageously used in a continuous process for the continuous production of oligomers from long-chain olefins. Such catalyst compositions can be used for prolonged periods without the need for regeneration. Nevertheless, with the passage of time, deactivation will tend to slowly occur. Deactivation can be measured qualitatively by the loss of olefin conversion, or as the increase of temperature required to maintain an essentially constant conversion rate for the olefin.

As an alternative approach for the preparation of the catalysts used in the present inventive process, a sulfate-activated Group IV oxide may be prepared by a one-step process, comprising heating a compound such as titanium sulfate hydrate at a temperature in the range of about 500° C. to about 625° C. Sulfate-activated zirconium dioxide compounds may be prepared in a similar manner using, for example, zirconium sulfate hydrate.

The oligomerization reaction may be carried out either batchwise, in a stirred slurry reactor, or continuously, in a fixed bed continuous flow reactor. The catalyst concentration should be sufficient to provide the desired catalytic effect. The temperatures at which the oligomerization may be performed are between about 50° and 300° C., with the preferred range being about 120° to 250° C., and the especially preferred range being about 160° to 180° C., for optimum conversion. At temperatures of about 200° C. or greater, the amount of unsaturation remaining in the products of the oligomerization reaction may decrease, thus reducing the degree of hydrogenation necessary to remove unsaturation from the base stocks. However, at temperatures above 200° C., the olefin conversion may decrease. The dimer to trimer ratio may increase. Applicants have found that the addition of a hydrocarbon containing a tertiary hydrogen, such as methylcyclohexane, may further reduce the amount of unsaturation present in the base stocks. One skilled in the art may choose the reaction conditions most suited to the results desired for a particular application. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

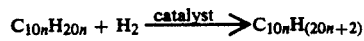

$$C_{10n}H_{20n} + H_2 \xrightarrow{\text{catalyst}} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the oligomers prior to hydrogenation and recycled to the catalyst bed for oligomerization. The removal or recycle of unreacted monomer or, if after hydrogenation, the removal of non-oligomerized alkane, should be conducted under mild conditions using vacuum distillation procedures known to those skilled in the art. Distillation at temperatures exceeding 250° C. may cause the oligomers to break down in some fashion and come off as volatiles. Preferably, therefore, the reboiler or pot temperature should be kept at or under about 225° C. when stripping out the monomer. Procedures known by those skilled in the art to be alternatives to vacuum distillation also may be employed to separate unreacted components from the oligomer.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The invention will be further illustrated by the following examples, which are given by way of illustration and not as limitations on the scope of this invention. The entire text of every patent, patent application or other reference mentioned above is hereby incorporated herein by reference.

EXAMPLES

In the examples detailed in Table I below, the following procedures were used:

Preparation of Catalysts

Titanium dioxide or zirconium dioxide extrudates (⅛) were charged to a crucible and covered with 10% ammonium sulfate solution. The pellets were allowed to stand for 15 minutes, then placed in an oven (with nitrogen purge) and heated slowly to the desired temperature for the desired time. The pellets were then cooled to less than 200° C. and placed in a tightly sealed glass bottle until just before use.

Oligomerization of Olefins

The catalyst pellets prepared above were ground to a fine powder. Olefin and catalyst were charged to a flask equipped with an overhead stirrer, thermometer, heating mantle, and a water-cooled condenser (N₂ purge). The mixture was vigorously stirred and heated to the desired temperature for the desired time. The mixture was then cooled to ambient temperature and filtered with suction. The liquid was analyzed by liquid chromatography. The results obtained are detailed in Table I.

TABLE I

USE OF PELLETED GROUP IV OXIDES ACTIVATED WITH SULFUR-CONTAINING COMPOUNDS TO OLIGOMERIZE OLEFINS

| Ex. No. | Olefin (by carbon number) | (g) of Olefin | Catalyst | Amount of Catalyst (g) | Time/Temp. (Hr)/(°C.) | Olefin Con. (%) | D/T+ Ratio |
|---|---|---|---|---|---|---|---|
| 1 | C-14 α | 100 | $TiO_2^{(a)}$ | 10 | 5/160 | ~0 | — |
| 2 | C-14 α | 100 | $TiO_2^{(a)}$ | 10 | 4/180 | ~0 | — |
| 3 | C-14 α | 100 | $TiO_2^{(b)}$ | 10 | 5/160 | ~0 | — |
| 4 | C-14 α | 100 | $TiO_2^{(b)}$ | 10 | 4/180 | 12.6 | — |
| 5 | C-14 α | 100 | $TiO_2^{(c)}$ | 10 | 5/160 | 2.0 | — |
| 6 | C-14 α | 100 | $TiO_2^{(d)}$ | 10 | 5/160 | 64.6 | 4.27 |
| 7 | C-14 α | 100 | $ZrO_2/SiO_2^{(e)}$ | 10 | 5/160 | ~0 | — |
| 8 | C-14 α | 100 | $ZrO_2^{(f)}$ | 10 | 5/160 | ~0 | — |
| 9 | C-14 α | 100 | $ZrO_2^{(g)}$ | 10 | 5/160 | 86.8 | 1.68 |
| 10 | C-14 α | 100 | $TiO_2^{(h)}$ | 10 | 5/160 | 31.0 | 12.4 |
| 11 | C-14 α | 100 | $ZrO_2^{(g)}$ | 10 | 4/180 | 78.6 | 2.32 |
| 12 | C-14 α | 100 | $TiO_2^{(h)}$ | 10 | 4/180 | 36.9 | 9.28 |
| 13 | C-10 α | 100 | $ZrO_2^{(g)}$ | 10 | 4/140 | 88.0 | 2.30 |
| 14 | C-10 α | 100 | $ZrO_2^{(g)}$ | 10 | 4/120 | 52.6 | 6.47 |
| 15 | C-10 α | 100 | $ZrO_2^{(g)}$ | 10 | 4/160 | 90.4 | 1.53 |
| 16 | C-14 α | 100 | $ZrO_2^{(i)}$ | 10 | 5/160 | 75.0 | 3.19 |

Con. = Conversion; D = Dimer; and T+ = Trimer + Tetramer + Pentamer, etc.
[a] Norton $TiO_2$ "as-is."
[b] $TiO_2$ calcined at 625° C. for 15 hours.
[c] $TiO_2$ treated with sulfuric acid and calcined at 300° C.
[d] $TiO_2$ treated with sulfuric acid and calcined at 625° C.
[e] $ZrO_2/SiO_2$ calcined at 625° C. for 15 hours.
[f] $ZrO_2$ calcined at 625° C. for 15 hours.
[g] $ZrO_2$ treated with 10% ammonium sulfate and heated at 625° C. for 15 hours.
[h] $TiO_2$ treated with 10% ammonium sulfate and heated at 625° C. for 15 hours.
[i] $ZrO_2$ treated with ammonium sulfate and heated at 750° C. for 15 hours.

In the examples detailed in Table II below, the following procedures were used:

One-Step Preparation of Catalysts

Titanium sulfate hydrate was calcined at 625° C. for 15 hours. Zirconium sulfate hydrate was treated in a similar manner.

Oligomerization of Olefins

Olefin and catalyst were charged to a flask equipped with an overhead stirrer, thermometer, heating mantle, and a water-cooled condenser ($N_2$ purge). The mixture was vigorously stirred and heated to the desired temperature for the desired time. The mixture was then cooled to ambient temperature and filtered with suction. The liquid was analyzed by liquid chromatography. The results obtained are detailed in Table II.

TABLE II

| Ex. No. | Olefin(s) (by carbon number) | (g) of Olefin | Catalyst | Amount of Catalyst (g) | Time/Temp. (Hr)/(°C.) | Olefin Con. (%) | D/T+ Ratio |
|---|---|---|---|---|---|---|---|
| 1 | C-14 α | 100 | $Ti(SO_4)_2 \cdot H_2O^1$ | 10 | 5/160 | 0.00 | — |
| 2 | C-14 α | 100 | $Ti(SO_4)_2 \cdot H_2O \cdot H_2SO_4$ | 10 | 5/160 | ~2 | — |
| 3 | C-14 α | 100 | $TiO_2^2$ | 10 | 5/160 | 36.4 | 14.3 |
| 4 | C-14 α | 100 | $TiO_2^2$ | 10 | 4/180 | 49.2 | 11.0 |
| 5 | C-10 α | 100 | $TiO_2^2$ | 10 | 5/160 | 64.0 | 5.57 |
| 6 | C-10 α | 100 | $TiO_2^2$ | 10 | 4/180 | 81.1 | 3.01 |
| 7 | C-1314i | 100 | $TiO_2^2$ | 10 | 4/180 | 37.6 | — |
| 8 | C-14 α | 84 | $ZrO_2^3$ | 8 | 5/160 | 85.9 | 1.81 |

Con. = Conversion; D = Dimer; and T+ = Trimer + Tetramer + Pentamer, etc.
[1] Not calcined.
[2] Prepared by heating titanium sulfate hydrate at 625° C. for 15 hours.
[3] $Zr(SO_4)_2 \cdot xH_2O$ calcined at 625° C.

We claim:

1. In a process for the preparation of oligomers from linear olefins containing from 10 to 24 carbon atoms, the improvement comprising oligomerizing said olefins in the presence of an oligomerization catalyst consisting essentially of sulfate-activated zirconium dioxide.

2. The process of claim 1, wherein the sulfate-activated zirconium dioxide is prepared by a two-step method comprising the steps of (a) treating zirconium dioxide with sulfuric acid or ammonium sulfate and (b) calcining the treated zirconium dioxide at a temperature of about 500° C. or greater.

3. The process of claim 1, wherein the sulfate-activated zirconium dioxide is prepared by a one-step method comprising heating zirconium sulfate hydrate at a temperature greater than about 500° C.

4. In a process for the preparation of oligomers from linear olefins containing from 10 to 24 carbon atoms, the improvement comprising oligomerizing said olefins at a temperature in the range of about 50° C. to about 300° C. and at a pressure of about atmospheric to about 1000 psig in the presence of an oligomerization catalyst consisting essentially of sulfate-activated zirconium dioxide.

5. The process of claim 4, wherein the olefins are oligomerized at a temperature in the range of about 120° C. to about 250° C.

6. The process of claim 4, wherein the olefins are oligomerized at a temperature in the range of about 160° C. to about 180° C.

7. The process of claim 4, wherein the sulfate-activated zirconium dioxide is prepared by a two-step method comprising the steps of (a) treating zirconium dioxide with sulfuric acid or ammonium sulfate and (b) calcining the treated zirconium dioxide at a temperature of about 500° C. or greater.

8. The process of claim 4, wherein the sulfate-activated zirconium dioxide is prepared by a one-step method comprising heating zirconium sulfate hydrate at a temperature greater than about 500° C.

9. The process of claim 4, wherein the olefins contain from 14 to 18 carbon atoms.

10. The process of claim 4, wherein the sulfate-activated zirconium dioxide has been calcined at a temperature of about 625° C. or greater.

11. In a process for the preparation of oligomers from linear olefins containing from 10 to 24 carbon atoms, the improvement comprising oligomerizing said olefins at a temperature in the range of about 50° C. to about 300° C. and at a pressure of about atmospheric to about 1000 psig in the presence of an oligomerization catalyst consisting of sulfate-activated zirconium dioxide, which sulfate-activated zirconium dioxide has been prepared by (1) treating zirconium dioxide with a sulfur-containing compound selected from the group consisting of ammonium sulfate, ammonium hydrogen sulfate, sulfuric acid, sulfur dioxide, sulfur trioxide, and hydrogen sulfide and (2) calcining said treated zirconium dioxide at a temperature greater than about 500° C.

12. The process of claim 11, wherein the sulfur-containing compound is selected from the group consisting of sulfuric acid and ammonium sulfate.

13. The process of claim 11, wherein the olefins are oligomerized at a temperature in the range of about 120° C. to about 250° C.

14. The process of claim 11, wherein the olefins are oligomerized at a temperature in the range of about 160° C. to about 180° C.

15. The process of claim 11, wherein the treated zirconium dioxide is calcined at a temperature of about 625° C. or greater.

* * * * *